United States Patent
Yamamoto et al.

(10) Patent No.: US 6,649,367 B2
(45) Date of Patent: Nov. 18, 2003

(54) HUMAN CANCER CELL LINE MALIGNANTLY ALTERED BY EXPRESSION OF ANGIOGENIC FACTOR

(75) Inventors: Yuji Yamamoto, Tukuba (JP); Yasuhiro Funahashi, New York, NY (US); Kenichi Nomoto, Tukuba (JP); Tatsuo Watanabe, Inzai (JP)

(73) Assignee: Eisai Co., Ltd, Tokyo (JP)

( * ) Notice: Subject to any disclaimer, the term of this patent is extended or adjusted under 35 U.S.C. 154(b) by 0 days.

(21) Appl. No.: 10/084,686

(22) Filed: Feb. 26, 2002

(65) Prior Publication Data

US 2003/0003580 A1 Jan. 2, 2003

(30) Foreign Application Priority Data

Mar. 22, 2001 (JP) ......................................... 2001-082819

(51) Int. Cl.[7] ............................ C12Q 1/02; C12Q 1/68; C12N 5/10
(52) U.S. Cl. ........................ 435/29; 435/325; 435/366; 435/6; 435/7.21; 435/7.8; 435/69.4; 435/703
(58) Field of Search ................................. 435/325, 366, 435/6, 7.21, 7.8, 29, 69.4, 70.3

(56) References Cited

FOREIGN PATENT DOCUMENTS

| JP | 2001-61483 | 3/2001 |
|---|---|---|
| WO | WO 97/34920 | * 9/1997 |

OTHER PUBLICATIONS

Yamamoto et al. Overexpression of VEGF or FGF–4 in human pancreatic cancer cells leads to different phenotype in orthoptic transplantation model. Mar. 2001, Proc. Am. Assoc. Cancer Res., vol. 42, pp. 821–822.*

Belletti et al. Modulation of in vivo growth of thyroid tumor–derived cell lines by sense and antisense vascular endothelial growth factor gene. 1999, Oncogene, Vol 18, pp. 4860–4869.*

McLeskey et al. Fibroblast growth factor 4 transfection of MCF–7 cells produces cell lines that are tumorogenic and metastatic in ovariectomized or tamoxifen–treated athymic nude mice. 1993, Cancer Res. vol. 53, pp. 2168–2177.*

McLeskey et al. Tumor growth of FGF or VEGF transfected MCF–7 breast carcinoma cells correlates with density of specific microvessels independent of the transfected angiogenic factor. 1998, Am. J. Pathol. vol. 153, pp. 1993–2006.*

Kadambi et al. Vascular endothelial growth factor (VEGF)–C differentially affects tumor vascular function and leukocyte recruitment: role of VEGF–receptor 2 and host VEGF–A. Mar. 2001, Cancer Res., Vol 61, pp. 2404–2408.*

* cited by examiner

Primary Examiner—James Ketter
Assistant Examiner—Daniel M. Sullivan
(74) Attorney, Agent, or Firm—Choate, Hall & Stewart; Brenda H. Jarrell; Charles F. Lyon

(57) ABSTRACT

A method for producing a cell to which angiogenesis-inducing ability has been imparted, comprising the steps of introducing a gene of an angiogenic factor into a human or animal cell having low angiogenesis-inducing ability, and selecting a cell that overexpresses the angiogenic factor; and a method for screening for an angiogenesis inhibitor or a substance having anticancer activity by using the produced cell.

6 Claims, 2 Drawing Sheets

HUMAN CANCER CELL LINE MALIGNANTLY ALTERED BY EXPRESSION OF ANGIOGENIC FACTOR

This application claims priority of Japanese Patent Application No. 2001-82819, filed Mar. 22, 2001.

BACKGROUND OF THE INVENTION

The present invention relates to a method for obtaining a malignant cell line, to a cell line obtainable by the method, to a method for screening for an angiogenesis inhibitor and an anticancer agent by using the obtained cell line, and to an angiogenesis inhibitor and an anticancer agent obtainable by the screening method.

In recent years, many reports have been made on the close relationship between the malignancy of a cancer (hematogenous metastasis, lymphogenous metastasis, dissemination, retention of cancerous ascites or pleural effusion, cancerous cachexia, and shortening of survival time of a host due to them) and angiogenesis (Macchiarini P, Fontanini G, Hardin M J, Squartini F, Angeletti C A, Lancet, 1992, Vol. 340, P145–146; Horak ER, Leek R, Klemk N, Lejeune S, Smith K, Stuart N, Greenall M, Steoniewska K, Harris A N, Lancet, 1992, Vol. 340, P1120–1124; Takahashi Y, Bucana CD, Cleary KR, Ellis LM, Int. J. Cancer, 1998, Vol. 79, P34–38). It has been reported that angiogenesis is induced by various angiogenic factors; and that among these factors, expressions of vascular endothelial growth factor (VEGF), platelet-derived growth factor, hepatocyte growth factor and fibroblast growth factor correlate with the prognosis of patients suffering from cancers. These suggest that angiogenesis induced by an angiogenic factor plays a key role in the malignant alternation of cancers.

Therefore, a model for evaluating the malignant alternation of cancers by an angiogenic factor can be a useful tool for the development of therapeutic agents for malignant tumors. Also, it can be a useful tool for the development of therapeutic agents for angiogenic diseases in which such angiogenic factors are involved.

Hitherto, the present inventors have reported on a model for directly evaluating VEGF-dependent hematogenous metastasis by introducing VEGF, which is one of angiogenic factors, into human colon carcinoma WiDr cells to increase the ability of metastasis (Funahashi et al., Jpn. J. Cancer Res., Vol. 90 Supplement, P132, 1999). However, since VEGF is not merely an angiogenic factor but also a vascular permeability factor and since WiDr cells conventionally have high angiogenesis-inducing ability, it is difficult to directly evaluate the introduced VEGF-dependent angiogenesis, and involvement of VEGF-dependent angiogenesis in the malignant alternation of cancers has not been elucidated yet.

As for cancers, while angiogenesis is a major factor for future aggravation, it is considered that many kinds of angiogenic factors are involved in angiogenesis induced by cancers.

SUMMARY OF THE INVENTION

In order to develop an effective anticancer agent that exhibits its effect by inhibition of angiogenesis, it must exhibit its effect not only on angiogenesis induced by VEGF but also on angiogenesis induced by various kinds of factors, and hence it is considered that evaluation of angiogenesis dependent on various angiogenic factors, in particular, evaluation of the effects on the malignant alternation of cancers based on the imparted angiogenic ability in respective organs is important. However, with conventional models, it has been difficult to sufficiently evaluate angiogenesis for an individual angiogenic factor.

Therefore, a main object of the present invention is to procure a cell which has acquired malignancy (hematogenous metastasis, lymphogenous metastasis, dissemination, retention of cancerous ascites or pleural effusion, cancerous cachexia, and shortening of survival time of a host due to them) as a result of increase in angiogenesis-inducing ability due to expression of an angiogenic factor, and further to establish a system for screening for an angiogenesis inhibitor and an anticancer agent by use of the cell.

The present inventors have introduced a gene of an angiogenic factor into a cell line having low in vivo angiogenesis-inducing ability to create a cell line having high angiogenic factor productivity. In addition, they have tried to create a model for evaluating the in vivo angiogenesis and the malignant alternation of cancers by use of the cell line having high angiogenic factor productivity.

As a result, it has been found that in the cell line having high angiogenic factor productivity, the in vivo angiogenesis ability is increased and further, increase in the ability of growth in a region of transplantation, increase in lymph node metastasis, retention of ascites, and shortening of survival time which is considered to be due to overall influences of these have been observed. Thus, it has been revealed that the introduced angiogenic factor alone induces angiogenesis and the malignant alternation of cancers.

Also, it has been revealed that cell lines having high angiogenic factor productivity differ in characteristics, dependent on the kind of angiogenic factors to be introduced, and they can serve as a model for evaluating the malignant alternation of cancers reflecting in vivo angiogenesis differing in the property depending on the variety of angiogenic factors and malignant tumors dependent on various angiogenic factors in clinical practices, so that they provide a useful tool for the development of therapeutic agents for malignant tumors and angiogenic diseases in clinical practices.

Based on the above findings, the present inventors have completed the present invention.

That is, the present invention provides the following.

(1) A method for producing a cell to which angiogenesis-inducing ability has been imparted, comprising the steps of an introducing a gene of angiogenic factor into a human or animal cell having low angiogenesis-inducing ability, and selecting a cell that overexpresses the angiogenic factor.

(2) The method according to (1), wherein the cell having low angiogenesis-inducing ability is human pancreatic cancer KP-1 cell.

(3) A method for screening for a substance having angiogenesis inhibitory activity, comprising the steps of bringing a candidate substance into contact with a cell obtained by the method as defined in (1) or (2), and selecting a substance having activity of inhibiting the angiogenesis-inducing ability of the cell.

(4) A method for producing an angiogenesis inhibitory composition, comprising the steps of obtaining a substance having angiogenesis inhibitory activity by the method as defined in (3), and preparing the composition from the obtained substance and a carrier.

(5) A method for screening for a substance having anti-cancer activity, comprising the steps of bringing a candidate substance into contact with a cell obtained by the method as defined in (1) or (2), and selecting a substance having anticancer activity on the cell.

(6) A method for producing an anticancer composition, comprising the steps of obtaining a substance having anticancer activity by the method as defined in (5), and preparing the composition from the obtained substance and a carrier.

According to the present invention, it has been elucidated that overexpression of angiogenic factors in less malignant cells, preferably KP-1 cells, results in increase in angiogenic ability and malignant alternation, and hence the present invention provides cells useful for examining the effect of angiogenic factors and enables screening for an angiogenesis inhibitor and an anticancer agent by use of such cells.

DETAILED DESCRIPTION OF THE INVENTION

Figure 1:
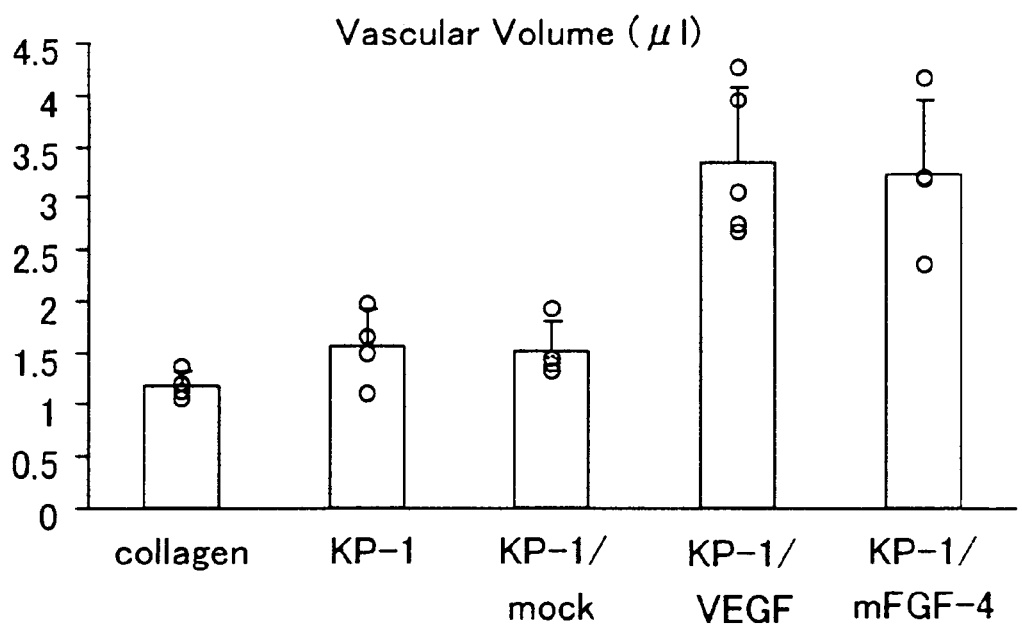
FIG. 1 shows comparison of in vivo angiogenesis-inducing activity.

Hereinafter, the present invention will be described in detail.

<1> Method for producing cells to which angiogenesis-inducing ability has been imparted and cells obtained by the method The cell-producing method of the present invention is a method for producing cells to which angiogenesis-inducing ability has been imparted, which is characterized by comprising the steps of introducing a gene of an angiogenic factor into a human or animal cell having low angiogenesis-inducing ability and selecting a cell that overexpresses an angiogenic factor.

The term "angiogenesis-inducing ability" used herein refers to activity of inducing angiogenesis. More specifically, it refers to activity of producing an angiogenic factor extracellularly. Such an activity can be measured by an ordinary method, preferably a method based on evaluation of in vivo angiogenesis, for example, a mouse dorsal air sac method (Advance in Medicine (Igaku no Ayumi), Vol. 122, No. 10, P890–894, 1982).

The term "cells to which angiogenesis-inducing ability has been imparted" used herein refers to cells having angiogenesis-inducing ability higher than that of an original cell to which an angiogenic factor gene is to be introduced.

The term "cells having low angiogenesis-inducing ability" used herein means cells that induce no significant angiogenesis as compared with the case where no cancer cell is present. Preferably, it means cells that induce no significant angiogenesis as measured by a method based on evaluation of in vivo angiogenesis, for example, a mouse dorsal air sac method (Advance in Medicine (Igaku no Ayumi), Vol. 122, No. 10, P890–894, 1982). Such cells are preferably established, i.e., cell lines. Specific examples thereof include human pancreatic cancer KP-1 cell, PSN-1 cell, Capan-1 cell, KP-3 cell, KP-4 cell, human lung cancer A549 cell, human colon cancer colo320DM cell, etc. It is preferred that the cell has a low degree of malignancy (malignancy degree). Also, it is preferred that the cell is high in the efficiency of transfection in consideration of easiness of introduction of an angiogenic factor gene, and for cases in which angiogenesis-inducing ability is to be measured, it is preferred that it has a low malignancy degree when orthotopic transplantation is performed in consideration of easiness of measurement of angiogenesis-inducing ability. Such a preferred cell may be exemplified by human pancreatic cancer KP-1 cell. KP-1 cell is available from Dr. Akira Funakoshi of National Kyushu Cancer Center (Ikeda, Y. et al., Jpn. J. Cancer Res., 81:987–993, 1990).

The term "malignancy" used herein refers to properties that cancer cells exhibit, such as angiogenesis-inducing ability, hematogenous metastasis, lymphogenous metastasis, dissemination, retention of cancerous ascites or pleural effusion, cancerous cachexia and shortening of survival time of the host based thereon, and the term "malignant alternation" refers to acquisition of such properties by cancer cells. Such properties can be measured by a method usually used for the evaluation of cancer cells.

The angiogenic factor is not particularly limited and examples thereof include growth factors such as VEGF, platelet-derived growth factor, hepatocyte growth factor, fibroblast growth factor, transforming growth factor-α, and epithelial growth factor (EGF), and cytokines such as interleukin 1 and interleukin 8.

The introduction of an angiogenic factor gene can be performed by a method usually used for introduction of a gene into human or animal cells. The angiogenic factor gene may be one that increases expression of an angiogenic factor when it is introduced into cells, and may be not in its full length.

The term "cells that overexpress an angiogenic factor" used herein refers to cells in which the expression of an angiogenic factor has increased higher than in original cells in which the angiogenic factor gene is to be introduced. The expression of an angiogenic factor can be measured by an ordinary method. For example, the expression of an angiogenic factor can be measured by measuring the angiogenic factor itself as a substance or by measuring its activity. Also, the expression of an angiogenic factor can be measured by the amount of mRNA that encodes the angiogenic factor.

Selection of cells that overexpress an angiogenic factor can be performed by a method usually used for the selection of transformants.

According to the present invention, human or animal cells having low angiogenesis-inducing ability are transformed by introducing therein a gene that encodes a specified factor such as VEGF to provide cells to which angiogenesis-inducing ability has been imparted by the specified factor. The obtained cells can be used for screening for an inhibitor that inhibits angiogenesis caused by the specified factor. Also, the obtained cells are preferably those cells malignantly altered by transformation with an angiogenic factor gene. Since such cells show malignancy by the expression of the angiogenic factor, they are useful in studying the mechanism of malignant alternation and also useful in screening for anticancer agents.

<2> Method for screening for a substance having angiogenesis inhibitory activity and a substance having anti-cancer activity, methods for producing an angiogenesis inhibitory composition and an anticancer composition, and an angiogenesis inhibitory composition and an anticancer composition obtained by the methods The method for screening for angiogenesis inhibiting substances according to the present invention is a method for screening for a substance having an angiogenesis inhibitory activity, which is characterized by comprising the steps of bringing a candidate substance into contact with the angiogenesis-inducing ability-imparted cell obtained by the above-mentioned production method according to the present invention, and selecting a substance having activity of inhibiting the angiogenesis-inducing ability of the cell.

The method for producing an angiogenesis inhibitory composition according to the present invention is characterized by comprising the steps of obtaining a substance having angiogenesis inhibiting activity by the method for screening for an angiogenesis inhibiting substance according to the present invention, and preparing the composition from the obtained substance and a carrier.

The method for screening for an anticancer substance according the present invention is a method for screening for a substance having an anticancer activity, which is characterized by comprising the steps of bringing a candidate substance into contact with the angiogenesis-inducing ability-imparted cell obtained by the above-mentioned production method according to the present invention, and selecting a substance having anticancer activity on the cell.

The method for producing an anticancer composition is characterized by comprising the steps of obtaining a substance having anticancer activity by the method for screening for an anticancer substance according to the present invention, and preparing the composition from the obtained substance and a carrier.

The screening methods of the present invention can be performed in the same manner as screening methods using ordinary cancer cells except for using angiogenesis-inducing ability-imparted cells as the cells to be screened. For example, contact of the candidate substances with the angiogenesis-inducing ability-imparted cells may be performed by a method usually used for bringing a substance such as drug into contact with human or animal cells. Also, the activity of inhibiting the angiogenesis-inducing ability of the angiogenesis-inducing ability-imparted cells or anticancer activity on the angiogenesis-inducing ability-imparted cells may be measured by a method usually used in the measurement of such activities.

Hereinafter, specific examples of the screening method are explained. However, the present invention is not limited thereto.

1. In vitro Screening for Anticancer Agents:

Usual in vitro screening of anticancer agents such as an MTT method (Alley MC, Scudiero DA, Monks A, Hursey ML, Czerwinski MJ, Fine DL, Abott BJ, Mayo JG, Shoemaker RH, Boyd MR, Cancer Res., 1988, Vol. 48, P589–601) and a colony formation method (Shoemaker RH, Wolpert-DeFilippes MK, Kern DH, Lieber MM, Makuch RW, Melnick NR, Miller WT, Salmon SE, Simon RM, Venditti JM, Cancer Res, 1985, Vol. 45, P2145–53) may be performed by use of angiogenesis-inducing ability-imparted cells, preferably those derived from KP-1 cell. By using of angiogenesis-inducing ability-imparted cells, preferably those derived from KP-1 cell, screening for an angiogenesis inhibitor that inhibits the angiogenesis induced by such cells and screening for an anticancer agent based on the inhibitory activity can be performed efficiently.

For example, by use of an in vitro lumen-forming model by co-culturing primary cultured human umbilical vein endothelial cells (HUVEC) with angiogenesis-inducing ability-imparted cells, preferably those derived from KP-1 cell, or by use of culture supernatant of angiogenesis-inducing ability-imparted cells, it is possible to evaluate the influence of a drug on angiogenesis induced by a cancer cell having acquired malignancy by overexpression of an angiogenic factor. Hereinafter, the methods will be described in detail. However, the present invention is not limited thereto.

One of such methods is a method for forming a collagen gel sandwich containing endothelial cells on cultured human angiogenesis-inducing ability-imparted cells. That is, a suitable cell number of angiogenesis-inducing ability-imparted cells, preferably those derived from KP-1 cell are inoculated on a culture dish, i.e., 24-well plate, and on the next day, collagen gel (for example, produced by Nitta Gelatin Co., Ltd.) is placed thereon and solidified at 37° C. Thereafter, HUVEC in a cell number that makes the cells confluent is inoculated and the cells are cultured in serum-free medium for HUVEC (GIBCO BRL) containing EGF overnight. On the next day, the culture solution was removed and again collagen gel is placed and solidified at 37° C. for about 4 hours to form collagen gel sandwich containing endothelial cells.

As an alternative method, a transwell chamber partitioned with transparent films may be placed on the cultured angiogenesis-inducing ability-imparted cells and a collagen gel sandwich containing endothelial cells may be formed.

On the solidified collagen gel, a serum-free medium for HUVEC containing EGF and a suitable concentration of a test drug are added and cultured under conditions of 5% $CO_2$ and 37° C. for 3 to 4 days, followed by evaluation of the effect of the drug on the formation of neovascularization network induced between the collagen gel layers.

2. In vivo screening for anticancer agents:

Since angiogenesis-inducing ability-imparted cells, preferably those derived from KP-1 cell undergo increase of neovascularization induction and malignant alternation by overexpression of an angiogenic factor, they can be transplanted into a test animal and the effects of an anticancer agent on angiogenesis induction and on malignant characteristics (hematogenous metastasis, lymphogenous metastasis, dissemination, retention of cancerous ascites or pleural effusion, cancerous cachexia and shortening of survival time of the host due to them) of transplanted cancer based on the angiogenesis induction can be evaluated.

The in vivo screening for an anticancer agent may include the following methods 1) to 4).

1) A method in which cells that overexpress an angiogenic factor are transplanted subcutaneously and the effect of an anticancer agent on growth of a tumor at the transplanted locus is observed.

2) A method in which cells that overexpress an angiogenic factor are enclosed in a chamber that can retain cells, which is fabricated with a porous film, the chamber is transplanted under dorsal skin of a test animal and the effect of an anticancer agent on neovascularization induced by the enclosed cells is observed. In this method, the effect of the test substance as an angiogenesis inhibitor can also be observed.

3) A method in which cells that overexpress an angiogenic factor are transplanted into a peripheral tissue, in particular a foot, of a test animal, and the effects of an anticancer agent on growth of a tumor, metastasis to lung, and survival time of the host are observed.

4) A method in which cells that overexpress an angiogenic factor are transplanted into the same locus where the cancer is emerged; that is, the orthotopic transplantation (in the case of pancreatic cancer cell lines, for example, pancreas is to be transplanted), and the effects of an anticancer agent on growth of a tumor at the transplanted locus, metastasis to lung, liver and lymph nodes, retention of cancerous ascites, occurrence of cancerous cachexia, and survival time of the host are observed.

Among these methods, the method 2) is an important method for directly evaluating the angiogenesis inhibitory effect. Also, for evaluation of anticancer agents, the orthotopic transplantation is a method that attracts attention since it can also generally give results that reflect clinical effects. Accordingly, hereinafter, detailed explanation will be made on the chamber transplantation method and orthotopic transplantation method as well as the method for evaluating anticancer agents. However, the present invention is not limited thereto.

2-1) Chamber Transplantation Model

Suspensions of angiogenesis-inducing ability-imparted cells, preferably those derived from KP-1 cell in a suitable concentration (for example, $3 \times 10^6$ cells/0.17 ml) are prepared and each suspension in a suitable amount (for example, 0.17 ml) is injected in a chamber fabricated by adhering a membrane (for example, 0.45-$\mu$m Durapore Filter Membrane (Millipore)) having a suitable pore size to a chamber ring (for example, one produced by Millipore) and sealed. An air sac having a suitable volume (for example, about 10 ml) is formed on dorsal subcutaneous portion of a suitable mouse (for example, 6-week-old female C57BL/6N mouse) under anesthesia and the chamber enclosing the cells is transplanted therein.

Four days after the transplantation, a suitable concentration (for example, 2,500,000 cpm/ml) of blood cell suspension prepared by labeling the cells with sodium chromate ($^{51}$Cr) or the like is injected in a suitable amount (for, example, 0.2 ml each) through the tail vein of the chamber-transplanted mouse, and then the skin portion contacting the chamber is cut out and the radioactivity thereof is measured by use of a $\gamma$-counter. From the measured radioactivity, the amount of blood is calculated and is used as an index of in vivo angiogenesis-inducing activity.

2-2) Orthotopic Transplantation Model

Angiogenesis inducing ability-imparted cells, preferably those derived from KP-1 cell are cultured, recovered by trypsin treatment and then a cell suspension at a suitable concentration (for example, about 5,000,000 cells/ml PBS) is prepared. About 1-cm cut is formed in the abdominal part of an immunodeficient mouse, preferably KSN nu/nu mouse or Balb/c nu/nu mouse anesthetized with 2.5% Avertin solution and the pancreas is carefully exposed. After injecting the cell suspension by use of, for example, a 27G-injection needle, the pancreas is returned into the abdominal cavity and the cut portion is sutured.

The efficacy of the anticancer agent can be evaluated by 1) Prolongation of survival time, 2) inhibition of growths of primary and inoculated tumors, 3) inhibition of metastasis, 4) inhibition of retention of cancerous ascites, and 5) inhibition of occurrence of cancerous cachexia, as described below.

1) Prolongation of Survival Time:

This is evaluated by a cumulative total number of dead mice.

2) Inhibition of Growths of Primary and Disseminated Tumors:

A tumor mass is excised from the pancreas, the weight of primary tumor is measured to evaluate the effect on the growth of primary tumor, all the tumors disseminated in the abdominal cavity are excised, and the weights of the disseminated tumors are measured to evaluate the effects on growth of disseminated tumors.

3) Inhibition of Metastasis:

After staining the taken-out liver with Bouin's fixative, the number of metastatic nodes of the liver is counted under a stereoscopic microscope to determine hematogenous metastasis. Also, lung metastasis is determined in a similar manner. Metastasis to mesenteric lymph nodes is observed under a stereoscopic microscope to evaluate lymphogenous metastasis. In any of these instances, analysis of pathological sections may be added as necessary.

4) Inhibition of Retention of Ascites:

Retention of ascites is observed with naked eye. In some cases, ascites is collected and the amount of VEGF existing therein is measured.

5) Inhibition of Cancerous Cachexia:

The body weight of a mouse into which a cancer has been transplanted is measured. In some cases, the function of liver or amount of fat is measured.

Preparation of the compositions from the substances obtained by the screening method as described above and a carrier can be performed by appropriately selecting preparation methods usually used depending on the property of the substance and use form of composition. The carrier is preferable a pharmaceutically acceptable carrier.

The administration route and dose of the angiogenesis inhibitor and the anticancer agent may be appropriately selected by a person skilled in the art. For example, administration of the anticancer agent is performed via various routes such as oral administration, intraperitoneal administration, and intravenous administration according to various administration schedules. These administration conditions may be selected appropriately depending on the drug so that the drug can be absorbed and a drug concentration sufficient for exhibiting efficacy can be maintained. Also, the dose is selected appropriately in consideration of antitumor activity and toxicity.

EXAMPLES

Hereinafter, the present invention will be described in more detail with reference to examples. However, the present invention is not limited thereto.

(1) Construction of VEGF Expression Vector

PCR was performed using a human placenta cDNA library (Toyobo) as a template and oligonucleotides having the nucleotide sequences shown by SEQ ID NOS: 1 and 2 as primers. After completion of the reaction, the 5'-terminal of the DNA was phosphorylated and an about 600 bp DNA band was separated on 1.2% agarose gel electrophoresis. After self-ligation, the DNA was cleaved with EcoRI and BamHI to recover a fragment, and then the fragment was inserted between the EcoRI site and the BamHI site of pUC19. This was introduced into *Escherichia Coli* JM83 and a plasmid (VPF4) harboring a VEGF gene was recovered from the transformed clone.

Then, VEGF gene was inserted in the multi-cloning site of pcDNA3.1(produced by Invitrogen) to obtain pcDNA3.1/VEGF.

(2) Creation of VEGF Overexpression Cell Line

After culturing human pancreatic cancer cell KP-1 ($3 \times 10^6$ cells) overnight, 3 Rg of pcDNA3.1/VEGF was introduced into the cells by use of Effectene Transfection Reagent kit (QIAGEN). The cells were cultured in 10% FCS-containing RPMI-1640 medium that contained 600 $\mu$g/ml of geneticin and drug-resistant cells were selected to obtain KP-1/VEGF. Also, KP-1/mock was obtained as a control in the same manner as above except that pcDNA3.1 was alternatively used in place of pcDNA3.1/VEGF.

(3) Measurement of the Amount of VEGF in the Supernatant of Culture Medium $5 \times 10^5$ cells/ml suspension of each of KP-1, KP-1/mock and KP-1/VEGF cells was prepared using 10% FCS-containing RPMI-1640 medium. 0.5 ml of each suspension was put in wells of a 24-well plate and cultured in a $CO_2$ incubator at 37° C. for 24 hours. Then, the supernatant was recovered and the amount of VEGF was determined by use of a VEGF measuring kit (Immuno Biology Institute Co., Ltd.).

As shown in Table 1, high-level production of VEGF was observed in KP-1/VEGF.

TABLE 1

Comparison of amount of VEGF in supernatant of culture solution

|  | KP-1 | KP-1/mock | KP-1/VEGF |
|---|---|---|---|
| VEGF (pg/ml) | 182.5 | 133.9 | 1628 |

(4) Construction of FGF-4 Expression Vector pBluescript plasmid in which murine FGF-4 cDNA (ATCC M30642) was introduced in an *E. coli* carrier was purified, cleaved with BamHI and ApaI to recover a resulting fragment, and then the fragument was inserted between the BamHI site and the ApaI site of pcDNA3.1. This was introduced into *E. coli* DH5a and a plasmid (pcDNA3.1/mFGF-4) was recovered from the transformed clone.

(5) Creation of FGF-4 Overexpression Cell Line

After culturing human pancreatic cancer cell KP-1 ($3 \times 10^6$ cells) overnight, 3 μg of pcDNA3.1/mFGF-4 was introduced into the cells by use of Effectene Transfection Reagent kit (QIAGEN). The cells were cultured in 10% FCS-containing RPMI-1640 medium that contained 600 μg/ml of Geneticin and drug-resistant cells were selected.

(6) Evaluation of In vivo Angiogenesis-Inducing Activity $3 \times 10^6$ cells/0.17 ml suspension of each of KP-1, KP-1/mock, KP-1/VEGF and KP-1/mFGF-4 cells was prepared using a collagen solution (a mixture of 3 mg/ml aqueous type I collagen solution, reconstituting buffer (produced by Nitta Gelatin Co., Ltd.), and ×5 concentrated RPMI-1640 medium in a volume ratio of 7:1:2). In a chamber formed by adhering 0.45-μm Durapore filter membrane (Millipore) to a chamber ring (Millipore), 0.17 ml of each suspension was injected through the injection inlet and sealed. An air sac of about 10 ml was formed on dorsal subcutaneous portion of a 6-week-old female C57BL/6N mouse under anesthesia and the chamber enclosing the cells therein was transplanted in the air sac.

Four days after the transplantation, 2,500,000 cpm/ml of blood cell suspension prepared by labeling the cells with sodium chromate ($^{51}Cr$) (Amersham Pharmacia) was injected in an amount of 0.2 ml each through the tail vein of the chamber-transplanted mouse, and then the skin portion contacting the chamber was cut out and the radioactivity thereof was measured by use of a γ-counter. From the measured radioactivity, the amount of blood (volume of blood vessel) was calculated and was used as an index of in vivo angiogenesis-inducing activity.

As shown in Table 2 and FIG. 1, in vivo angiogenesis-inducing activity was observed in KP-1/VEGF and KP-1/mFGF-4 with respect to KP-1/mock. In Table 2 and FIG. 1, "collagen" indicates the case where the collagen solution only was used.

TABLE 2

Comparison of in vivo angiogenesis-inducing activity

|  | Collagen | KP-1 | KP-1/mock | KP-1/VEGF | KP-1/mFGF-4 |
|---|---|---|---|---|---|
| Volume of blood vessel (μl) | 1.19 ± 0.13 | 1.56 ± 0.36 | 1.52 ± 0.27 | 3.34 ± 0.73 | 3.23 ± 0.73 |

(7) Evaluation of Tumor Growth Using Subcutaneous Transplantation Model $5 \times 10^5$ cells/ml suspension of each of KP-1/mock, KP-1/VEGF and KP-1/mFGF-4 cells was prepared using PBS, and 0.1 ml of each suspension was subcutaneously transplanted to the right flank of a 6-week-old female balb/c nu/nu mouse.

From the time when the volume of tumor reached about 100 mm³, the volume of tumor was measured once a week. The volume of tumor was obtained by measuring the major axis diameter and the minor axis diameter of the tumor by use of a caliper and calculating the value of ½(major axis diameter×minor axis diameter×minor axis diameter).

Figure 2:
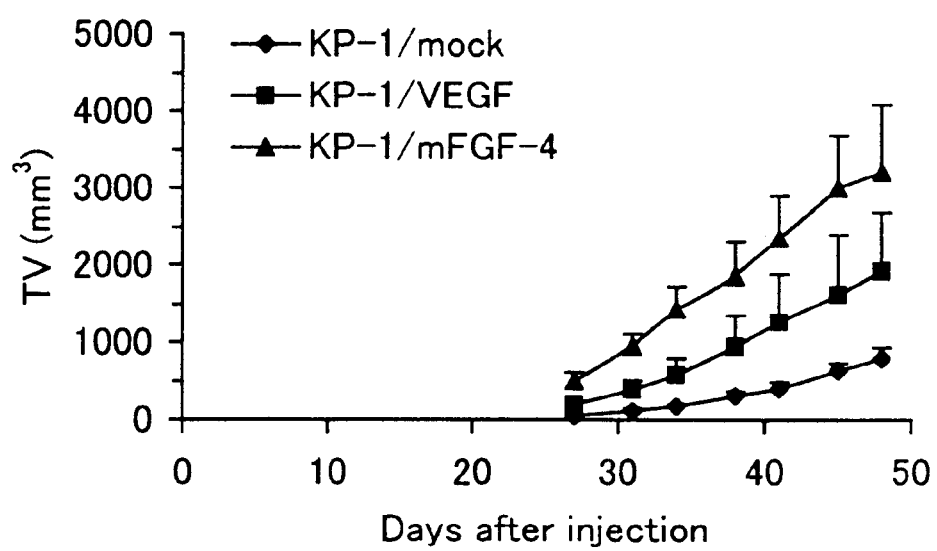
FIG. 2 shows comparison of growth of tumors by use of a subcutaneous transplantation model.

As shown in Table 3 and FIG. 2, KP-1/VEGF and KP-1/mFGF-4 showed tumor growths of about 2 times and about 4 times faster than that of KP-1/mock, respectively.

TABLE 3

Comparison of tumor growth using a subcutaneous transplantation model

|  | KP-1/mock | KP-1/VEGF | KP-1/mFGF-4 |
|---|---|---|---|
| Tumor volume 48 days after transplantation | 791.9 ± 136.5 | 1908.8 ± 790.1 | 3208.0 ± 880.5 |

(8) Evaluation of Tumor Growth, Retention of Cancerous Ascites and Survival Time Using Orthotopic Transplantation Model $7 \times 10^7$ cells/ml suspension of each of KP-1/mock, KP-1/VEGF and KP-1/mFGF-4 cells was prepared using PBS. Under anesthesia, a 6-week-old female balb/c nu/nu mouse was subjected to ventrotomy and 0.1 ml of each suspension was transplanted into the head of pancreas and the incision was sutured.

28 days after the transplantation, the tumor mass was excised from the pancreas and the weight of primary tumor was measured.

As shown in Table 4, KP-1/VEGF and KP-1/mFGF-4 showed tumor growths of about 2 times and about 3 times faster than that of KP-1/mock, respectively.

In addition, retention of cancerous ascites of murine similarly subjected to the orthotopical transplantation was observed with naked eye. Furthermore, a cumulative total number of dead mice was obtained to evaluate survival time.

Figure 3:
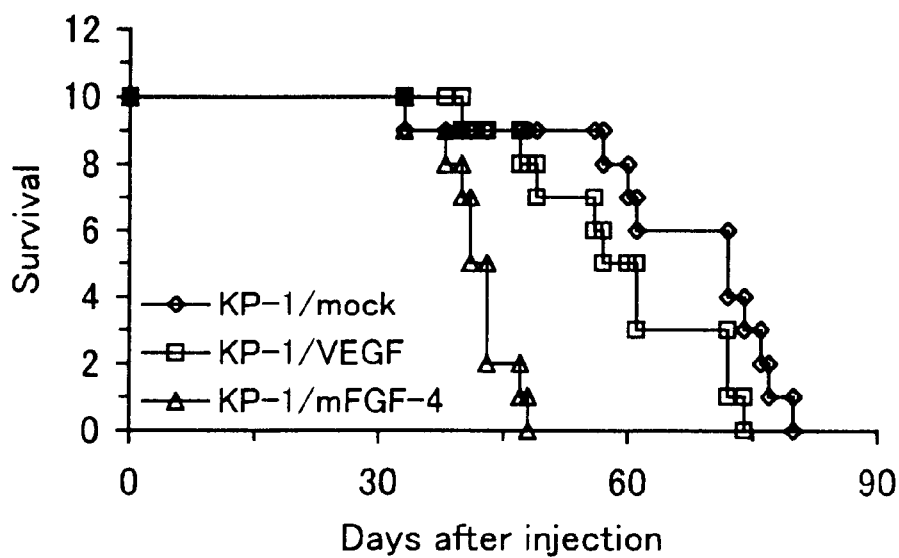
FIG. 3 shows comparison of retention of cancerous ascites and survival time by use of an orthotopic transplantation model.

As shown in Table 5 and FIG. 3, retention of ascites was observed in each of KP-1/mock-, KP-1/VEGF-and KP-1/mFGF-4-transplanted mice. The survival time of KP-1/VEGF- or KP-1/mFGF-4-transplanted mice was shortened as compared with KP-1/mock-transplanted mice.

TABLE 4

Comparison of tumor growth using an orthotopic translation model

|  | KP-1/mock | KP-1/VEGF | KP-1/mFGF-4 |
|---|---|---|---|
| Tumor weight 28 days after transplantation (mg) | 424.4 ± 170.7 | 820.6 ± 118.2 | 1040.4 ± 127.2 |
| (Range) | (124–551) | (657–947) | (874–1199) |

TABLE 5

Comparison of retention of cancerous ascites and survival time using an orthotopic transplantation model

|  | KP-1/mock | KP-1/VEGF | KP-1/mFGF-4 |
|---|---|---|---|
| Median survival time (day) | 72 | 59 | 42 |
| (Range) | (33–80) | (40–74) | (33–48) |
| Retention of ascites | 7/10 | 8/10 | 10/10 |

(9) Effects of VEGFR Kinase Inhibitor and EGFR Kinase Inhibitor on In vivo Angiogenesis Induced by KP-1/VEGF $3 \times 10^6$ cells/0.17 ml suspension of KP-1/VEGF cells was prepared using a collagen solution. In a chamber formed by adhering 0.45-μm Durapore filter membrane (Millipore) to a chamber ring (Millipore), 0.17 ml of the suspension was injected through the injection inlet and sealed. An air sac of about 10 ml was formed on dorsal subcutaneous portion of a 6-week-old female C57BL/6N mouse under anesthesia and the chamber enclosing the cells therein was transplanted in the air sac.

From the day of transplantation, ZD6474 as a VEGFR kinase inhibitor and ZD1839(Iressa) as an EGFR kinase inhibitor were each orally administered in dosage of 25, 50 or 100 mg/kg once a day for 4 days.

Four days after the transplantation, 2,500,000 cpm/ml of blood cell suspension prepared by labeling the cells with sodium chromate ($^{51}$Cr) (Amersham Pharmacia) was injected in an amount of 0.2 ml each through the tail vein of the chamber-transplanted mouse, and then the skin portion contacting the chamber was cut out and the radioactivity thereof was measured by use of a γ-counter. From the measured radioactivity, the amount of blood (volume of blood vessel) was calculated and was used as an index of in vivo angiogenesis-inducing activity.

Further, providing that the in vivo angiogenesis-inducing activity of control is A, the in vivo angiogenesis-inducing activity of collagen is B, and the in vivo angiogenesis-inducing activity of each administered group is X, in vivo angiogenesis inhibitory effect was obtained by the following equation. In vivo angiogenesis inhibitory effect (%)

$$=(X-B)/(A-B) \times 100$$

Figure 4:
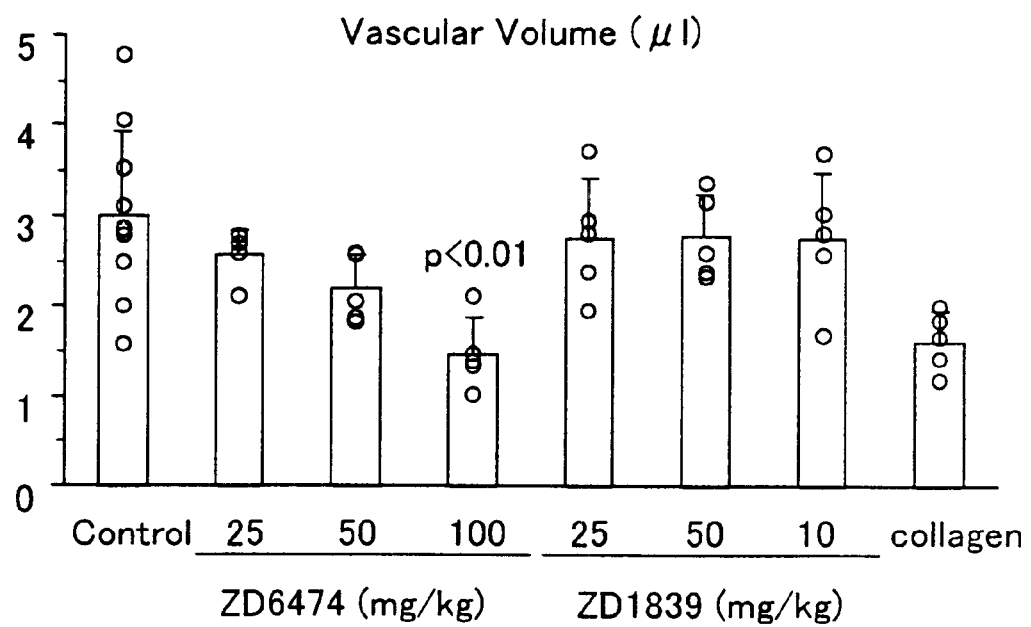
FIG. 4 shows the effects of a VEGFR kinase inhibitor and an EGFR kinase inhibitor on in vivo angiogenesis induced by KP-1/VEGF.

As shown in FIG. 4 and Table 6, the in vivo angiogenesis induced by KP-1/VEGF was inhibited by ZD6474, a VEGFR kinase inhibitor, but was not inhibited at all by ZD1839, an EGFR kinase inhibitor. The above results indicate that the in vivo angiogenesis induced by KP-1/VEGF is VEGF-dependent.

TABLE 6

Effects of VEGFR kinase inhibitor and EGFR kinase inhibitor

| Dose | (mg/kg) | In vivo angiogenesis-inducing activity (μl) | In vivo angiogenesis inhibitory effect (%) |  | n |
|---|---|---|---|---|---|
| Control | / | 3.00 ± 0.94 | / |  | 10 |
| ZD6474 | 25 | 2.56 ± 0.26 | 68.0 |  | 5 |
|  | 50 | 2.18 ± 0.38 | 40.8 |  | 5 |
|  | 100 | 1.47 ± 0.40 | −10.9 | p < 0.01 | 5 |
| ZD1839 | 25 | 2.75 ± 0.66 | 82.2 |  | 5 |
|  | 50 | 2.77 ± 0.47 | 83.2 |  | 5 |
|  | 100 | 2.76 ± 0.73 | 82.5 |  | 5 |
| Collagen | / | 1.62 ± 0.33 | / |  | 5 |

What is claimed is:

1. A method for screening for a substance having angiogenesis inhibitory activity, comprising the steps of bringing a candidate substance into contact with a cell, having angiogenesis-inducing ability, and selecting a substance having activity of inhibiting the angiogenesis-inducing ability of the cell, wherein said cell is a cell to which angiogenesis-inducing ability has been imparted by introducing a gene of an angiogenic factor selected from the group consisting of vascular endothelial growth factor, platelet-derived growth factor, hepatocyte growth factor, fibroblast growth factor, transforming growth factor-α, epithelial growth factor, interleukin 1 and interleukin 8, into a tumorigenic human or animal cancer cell having low angiogenesis-inducing ability, and selecting a cell that overexpresses the angiogenic factor.

2. A method for producing an angiogenesis inhibitory composition, comprising the steps of obtaining a substance having angiogenesis inhibitory activity the method of bringing a candidate substance into contact with a cell, having angiogenesis-inducing ability, and selecting a substance having activity of inhibiting the angiogenesis-inducing ability of the cell, wherein said cell is a cell to which angiogenesis-inducing ability has been imparted by introducing a gene of an angiogenic factor selected from the group consisting of vascular endothelial growth factor, platelet-derived growth factor, hepatocyte growth factor, fibroblast growth factor, transforming growth factor-α, epithelial growth factor, interleukin 1 and interleukin 8, into a tumorigenic human or animal cancer cell having low angiogenesis-inducing ability, and selecting a cell that overexpresses the angiogenic factor, and preparing the composition from the obtained substance and a carrier.

3. A method for screening for a substance having anticancer activity, comprising the steps of bringing a candidate substance into contact with a cell, and selecting a substance having anticancer activity on the cell, wherein said cell is a cell to which angiogenesis-inducing ability has been imparted by introducing a gene of an angiogenic factor selected from the group consisting of vascular endothelial growth factor, platelet-derived growth factor, hepatocyte growth factor, fibroblast growth factor, transforming growth factor-α, epithelial growth factor, interleukin 1 and interleukin 8, into a tumorigenic human or animal cancer cell having low angiogenesis-inducing ability, and selecting a cell that overexpresses the angiogenic factor.

4. A method for producing an anticancer composition, comprising the steps of obtaining a substance having anticancer activity by the method of bringing a candidate substance into contact with a cell, and selecting a substance having anticancer activity on the cell, wherein said cell is a cell to which angiogenesis-inducing ability has been imparted by introducing a gene of an angiogenic factor selected from the group consisting of vascular endothelial growth factor, platelet-derived growth factor, hepatocyte growth factor, fibroblast growth factor, transforming growth factor-α, epithelial growth factor, interleukin 1 and interleukin 8, into a tumorigenic human or animal cancer cell having low angiogenesis-inducing ability, and selecting a cell that overexpresses the angiogenic factor, and preparing the composition from the obtained substance and a carrier.

5. A method for screening for a substance having angiogenesis inhibitory activity, comprising the steps of:

introducing a gene of an angiogenic factor selected from the group consisting of vascular endothelial growth factor, platelet-derived growth factor, hepatocyte growth factor, fibroblast growth factor, transforming growth factor-α, epithelial growth factor, interleukin 1 and interleukin 8, into a tumorigenic human or animal cancer cell having low angiogenesis-inducing ability, selecting a cell that overexpresses the angiogenic factor, bringing a candidate substance into contact with the cell, and selecting a substance having activity of inhibiting the angiogenesis-inducing ability of the cell.

6. A method for screening for a substance having anticancer activity, comprising the steps of:

introducing a gene of an angiogenic factor selected from the group consisting of vascular endothelial growth factor, platelet-derived growth factor, hepatocyte growth factor, fibroblast growth factor, transforming growth factor-α, epithelial growth factor, interleukin 1 and interleukin 8, into a tumorigenic human or animal cancer cell having low angiogenesis-inducing ability, selecting a cell that overexpresses the angiogenic factor, bringing a candidate substance into contact with the cell, and selecting a substance having anticancer activity on the cell.

* * * * *

UNITED STATES PATENT AND TRADEMARK OFFICE
CERTIFICATE OF CORRECTION

PATENT NO. : 6,649,367 B2
DATED : November 18, 2003
INVENTOR(S) : Yamamoto et al.

It is certified that error appears in the above-identified patent and that said Letters Patent is hereby corrected as shown below:

<u>Column 13,</u>
Lines 13-14, "a candidate substance into contact with a cell, having angiogenesis-inducing ability, and selecting a substance" should read as --a candidate substance into contact with a cell, and selecting a substance --.
Line 28, "having angiogenesis inhibitory activity the method of bringing" should read as -- having angiogenesis inhibitory activity by the method of bringing --.
Lines 29-30, "a candidate substance into contact with a cell, having angiogenesis-inducing ability, and selecting a substance" should read as -- a candidate substance into contact with a cell, and selecting a substance --.
Line 42, "composition from the obtained substance and a carner" should read as -- composition from the obtained substance and a carrier --.

Signed and Sealed this

Thirteenth Day of July, 2004

JON W. DUDAS
*Acting Director of the United States Patent and Trademark Office*

SEQUENCE LISTING

<160> NUMBER OF SEQ ID NOS: 2

<210> SEQ ID NO 1
<211> LENGTH: 23
<212> TYPE: DNA
<213> ORGANISM: Artificial Sequence
<220> FEATURE:
<223> OTHER INFORMATION: primer

<400> SEQUENCE: 1
ccggatccat gaactttctg ctg                                    23

<210> SEQ ID NO 2
<211> LENGTH: 21
<212> TYPE: DNA
<213> ORGANISM: Artificial Sequence
<220> FEATURE:

-continued

<223> OTHER INFORMATION: primer

<400> SEQUENCE: 2
gtgaattctg tatcgatcgt t    21